(12) United States Patent
Weiler et al.

(10) Patent No.: US 10,858,133 B2
(45) Date of Patent: Dec. 8, 2020

(54) METHOD AND DEVICE TO STERILISE CONTAINERS

(71) Applicant: SIG Technology AG, Neuhausen am Rheinfall (CH)

(72) Inventors: Christian Weiler, Geldern (DE); Hanno Geissler, Krefeld (DE); Hans-Willi Mainz, Heinsberg (DE); Sittipong Boonkaew, Chonburi (TH)

(73) Assignee: SIG Technology AG, Neuhausen am Rheinfall (CH)

( * ) Notice: Subject to any disclaimer, the term of this patent is extended or adjusted under 35 U.S.C. 154(b) by 303 days.

(21) Appl. No.: 15/536,376

(22) PCT Filed: Dec. 4, 2015

(86) PCT No.: PCT/EP2015/078618
§ 371 (c)(1),
(2) Date: Jun. 15, 2017

(87) PCT Pub. No.: WO2016/096472
PCT Pub. Date: Jun. 23, 2016

(65) Prior Publication Data
US 2017/0341791 A1  Nov. 30, 2017

(30) Foreign Application Priority Data
Dec. 16, 2014  (DE) .................. 10 2014 118 776

(51) Int. Cl.
*B65B 55/10* (2006.01)
*A61L 2/18* (2006.01)
(Continued)

(52) U.S. Cl.
CPC ............ *B65B 55/10* (2013.01); *A61L 2/18* (2013.01); *A61L 2/208* (2013.01); *B65B 55/027* (2013.01);
(Continued)

(58) Field of Classification Search
CPC ............ A61L 2/208; A61L 2/18; B65B 55/10
See application file for complete search history.

(56) References Cited

U.S. PATENT DOCUMENTS 4,296,068 A * 10/1981 Hoshino ................. B65B 55/10
134/18
4,992,247 A * 2/1991 Foti ........................... A61L 2/20
422/28
(Continued)

FOREIGN PATENT DOCUMENTS

| CN | 1498119 A | 5/2004 |
| CN | 102459007 A | 5/2012 |

(Continued)

*Primary Examiner* — Sean E Conley
(74) *Attorney, Agent, or Firm* — The Webb Law Firm

(57) ABSTRACT

Described and illustrated is a method to sterilise containers or receiving flowable foods in a filling device. The method includes evaporating a hydrogen peroxide solution in an evaporator impinging at least one container with the vaporous hydrogen peroxide in a sterilisation zone and at least partially removing the unconsumed part of the vaporous hydrogen peroxide from the sterilisation zone. The removed vaporous hydrogen peroxide is at least partially condensed in a condenser and the condensed hydrogen peroxide is supplied to the evaporator.

13 Claims, 2 Drawing Sheets

(51) Int. Cl.
*A61L 2/20* (2006.01)
*B65B 55/02* (2006.01)
*B67C 7/00* (2006.01)
*B65B 3/02* (2006.01)

(52) U.S. Cl.
CPC ......... *B67C 7/0073* (2013.01); *A61L 2202/11* (2013.01); *A61L 2202/23* (2013.01); *B65B 3/025* (2013.01)

(56) References Cited

U.S. PATENT DOCUMENTS 9,034,253 B2    5/2015  Geissler
2014/0291320 A1* 10/2014  Floerke ................. B65D 59/04
                                              220/62

FOREIGN PATENT DOCUMENTS

| DE | 19945500 A1 | 4/2000 |
|---|---|---|
| EP | 0361858 A1 | 4/1990 |
| JP | S5670768 A | 6/1981 |
| JP | S6239431 A | 3/1992 |
| JP | H1147242 | 2/1999 |

\* cited by examiner

METHOD AND DEVICE TO STERILISE CONTAINERS

CROSS-REFERENCE TO RELATED APPLICATIONS

This application is the United States national phase of International Application No. PCT/EP2015/078618 filed Dec. 4, 2015, and claims priority to German Patent Application No. 10 2014 118 776.8 filed Dec. 16, 2014, the disclosures of which are hereby incorporated in their entirety by reference.

BACKGROUND OF THE INVENTION

Field of the Invention

The invention relates to a method to sterilise containers for, in particular flowable foods in which a hydrogen peroxide solution is evaporated in an evaporator, in which at least one container is impinged with the vaporous hydrogen peroxide in a sterilisation zone, in which the unconsumed part of the vaporous hydrogen peroxide is at least partially removed from the sterilisation zone. Furthermore, the invention relates to a device to sterilise containers for, in particular, flowable foods, preferably to implement the method referred to, having a sterilisation zone to sterilise at least one container, an evaporator to evaporate a hydrogen peroxide solution, a sterilisation device to impinge the at least one container with vaporous hydrogen peroxide in the sterilisation zone and a removal device to at least partially remove the unconsumed part of the vaporous hydrogen peroxide from the sterilisation zone.

Description of Related Art

Methods to sterilise containers for foods are known in various embodiments. The sterilisation and the filling of the containers with, preferably flowable foods therein frequently occur in an aseptic environment by one and the same device which is therefore mostly referred to as a filling machine.

To fill containers with, in particular flowable foods on an industrial scale, so-called filling machines are used. As the foods should be able to be kept for a long time after the filling and closing of the containers, a filling which is as sterile as possible is desirable. For this purpose, the filling machines have sterilisation areas or aseptic chambers in which the containers are sterilised and subsequently are filled and closed under conditions which are as sterile as possible.

Frequently packages are used therein as food containers which are open on their upper side in order to provide an opening for filling. The packages can, for example, be cardboard composite packages which are formed from a laminate comprising a cardboard layer and outer plastic layers, in particular polyethylene (PE). The cardboard provides the packages with a sufficient stability so that the packages can be simply handled and, for example, stacked. The plastic layers protect the cardboard from moisture and the food from absorption of undesired material from the package. Additionally, further layers, such as, for example, an aluminium layer, can be provided which reduce a diffusion of oxygen and other gases through the package.

The packages can be produced, preferably in the filling machine, from a precursor package. For example, cut-to-size packaging material can be used as a precursor package which can be pre-assembled if necessary, and indeed for example by sealing the longitudinal edges to form a packaging material blank. Alternatively, the package material used for the precursor package can be unwound practically infinitely from a roll. In the case of cut-to-size packaging material, this is folded at bend lines in order to initially form a package cover and a package base. The package cover and the package base are closed by sealing overlapping sections of the packaging material. The head of the package initially still remains open. The package head can also initially be closed if necessary and the package can be filled through the base which is still open and is preferably pointing upwards.

Subsequently, the packages are supplied into a sterilisation zone of the filling machine. This mostly occurs by the packages being passed one after the other to cells of a transport chain which receive the packages. The transport chain then ensures that the packages are transported at a defined speed and at a defined distance from each other through the sterilisation zone of the filling machine.

The packages are initially preheated in the sterilisation zone. Then the containers are blasted with hot sterilised air. Subsequently, the containers are sterilised. In addition, an aqueous hydrogen peroxide solution is evaporated in an evaporator. The vapour made from water and hydrogen peroxide is then sprayed into the preheated packages, wherein the inner surface of the entire package container and at least the head region of the outer surface is impinged with the hydrogen peroxide. The hydrogen peroxide reacts with the microorganisms present and kills these. This occurs more quickly and with less condensation if the containers are preheated. Subsequently, a drying of the sterilised packages with sterilised air occurs, after which the package is passed into the filling and sealing zone and there is finally filled with a food. The food is therein preferably flowable. In a plurality of cases, the food products are drinks. Subsequently, the filled package is closed again before the closed package is transported from the filling and sealing zone via the transport chain. The sterilisation zone is open downwards in partial regions, and ends at the height of the non-sterile transport chain or below this. The mixture of sterilised air, stream and residual hydrogen peroxide is therefore removed and led away at the lower end of the sterilisation zone.

A so-called aseptic zone is formed in the filling and sealing zone. The aseptic zone refers to the actually aseptic region in the upper section of the filling and sealing zone. The aseptic chamber comprises the sterilisation zone as well as the filling and sealing zone. The aseptic chamber can be formed according to the type of a housing, wherein openings to supply and guide away packages are provided. Additionally, the aseptic chamber can have at least one opening at the lower end in order to remove the atmosphere from the sterilisation zone and/or the filling and sealing zone. The area underneath the aseptic chamber is not aseptic, which, however, does not impair the aseptic filling of the package.

The hydrogen peroxide which is not converted in the sterilisation zone is not reused. Until now the reutilisation of hydrogen peroxide has always been considered as technically too laborious and not economical. It has therefore only been attempted to reduce the quantity of hydrogen peroxide used. The hydrogen peroxide is therefore supplied to an exhaust gas cleaning system with other process exhaust gases, depending on the respective requirements. The loss of hydrogen peroxide resulting in this manner is, however, not inconsiderable over time. Furthermore, the hydrogen peroxide can affect the system technology for exhaust gas treatment and/or for transporting the exhaust gas away due to its high reactivity and oxidative effect, for which reason mostly materials are used which are not affected by or only slightly affected by hydrogen peroxide.

SUMMARY OF THE INVENTION

An object of the present invention is to design and to develop the method and the device, each of the type referred to at the beginning, in such a way that an overall more economical operation is possible.

This object is achieved by a method disclosed herein in which the removed vaporous hydrogen peroxide is at least partially condensed in a condenser and the condensed hydrogen peroxide is supplied to the evaporator again.

The object referred to is furthermore achieved by a device disclosed herein in that a condenser is provided to at least partially condense the removed vaporous hydrogen peroxide and a supply unit is provided to supply the condensed hydrogen peroxide to the evaporator.

The invention has also recognised that an economical reutilisation at least of parts of the over-stoichiometrically used hydrogen peroxide is possible in the sense of a recirculation. This is the case despite the typically high energy use for condensation, in particular of gases containing water vapour. Additionally, the invention has recognised that the reduced reactivity and self-decomposition of the hydrogen peroxide in the condensate can be used to increase the yield. Alternatively or additionally, the condensate does not have to be reused directly, but can initially be supplied to a conditioning system without a notable loss of hydrogen peroxide.

A further advantage of the invention lies in that, due to the process parameters of the condensation, in particular the temperature, either the hydrogen peroxide concentration can be increased or the hydrogen peroxide loss can be reduced via the gas phase. The lower the hydrogen peroxide loss, the higher the so-called hydrogen peroxide yield or recovery rate. Therefore, for example, hydrogen peroxide concentrations can be implemented in the condensate which amount to between 10% by weight and 70% by weight. Preferably, the hydrogen concentration amounts to between 20% by weight and 60% by weight, in particular between 25% by weight and 40% by weight. The recovery rate of the hydrogen peroxide can amount to between 10% and 70% of the hydrogen peroxide supplied to the condenser. Preferably, the recovery rate, however, amounts to between 20% and 60%, in particular between 30% and 50%. Alternatively or additionally, the hydrogen concentration can be adjusted after the condensation by concentration or thinning of the condensate to a value between 30% by weight and 40% by weight, in particular for example to 35% by weight.

In order to increase the volume of the sterilisation gas blown onto the package, this preferably consists of a treatment agent comprising water vapour and hydrogen peroxide as well as proportions of, in particular filtered, air, preferably pressurised air. Therefore, an even contact is achieved between the container and the hydrogen peroxide without increased quantities of hydrogen peroxide having to be used.

The hydrogen peroxide solution, for the sake of simplicity, can therein alternatively or additionally be evaporated in an electrically heated evaporator. Then it is possible without any problems to provide heated contact surfaces for the hydrogen peroxide at a high temperature level. The contact surfaces are therein preferably provided by heating resistors which are connected to a voltage supply. So that the evaporation of the hydrogen peroxide can expediently occur in an evaporator, the filtered air, in particular filtered pressured air, can initially be mixed with the hydrogen peroxide solution before the mixture of hydrogen peroxide solution and air is evaporated in the evaporator. This can, for example, occur in a type of nozzle in which the sterilised air can be used as a carrier gas for application to the container and/or for swirling as well as mixing the hydrogen peroxide.

A sterilised container at least substantially without microorganisms on the inner surface is particularly suitable to fill with foods which should be flowable, in particular liquid, for easy filling. Therefore, no entry of microorganisms into the containers is desirable between the sterilisation and filling. Against this background, it is preferred if the sterilised container is also filled in the same device. Lastly, it is also particularly preferred if the device is a filling machine and/or the method also comprises the step of filling the at least one sterilised container.

The sterilisation zone comprises at least the region in which the container to be sterilised is impinged with vaporous hydrogen peroxide by means of a sterilisation device in order to kill microorganisms. If necessary, however, further method steps occur in the sterilisation zone which can accompany the introduction of further media via corresponding entrances to the sterilisation zone. Additionally, the sterilisation zone together with a filling zone and/or a sealing zone can be parts of an aseptic chamber. To prevent a contamination of the filled product, the aseptic chamber comprises a filling and sealing zone next to the sterilisation zone. Therein, the transport of the container and the implementation is simplified if the sterilisation zone and the filling and sealing zone are adjacent to each other. In order to reduce the risk of an entry of microorganisms from the sterilisation zone into the filling and sealing zone, a structural constriction can be provided between the sterilisation zone on the one and hand and the filling and sealing zone on the other hand, which can if necessary only be a little wider than the container which is to be transported from the sterilisation zone into the filling and sealing zone through the constriction. Alternatively or additionally, the sterilisation zone can be separated from the filling and sealing zone by a so-called curtain which is formed by an, in particular laminar, flow of sterilised air. The sterilised air therein preferably flows from top to bottom in order to prevent the entry of microorganisms into the filling and sealing zone. The sterilised air can, for the sake of simplicity, be filtered air. The air is filtered, for example by means of membranes, so finely that the microorganisms present in the raw air are separated to the extent that the remaining air can be considered to be sterile.

Subsequently, for the sake of simpler understanding and to prevent unnecessary repetitions, preferred embodiments of the method and of the device are described together without differentiating in detail between the method and the device respectively. Each of the preferred features with regard to the method and with regard to the device, however, nevertheless result for the person skilled in the art.

In a first preferred embodiment of the invention, sterilised air is supplied to the sterilisation zone of the device. This can help prevent the introduction of germs and similar into the sterilisation zone, in particular by the formation of a sterile flow of air, water vapour and hydrogen peroxide through the sterilisation zone, and indeed in particular from top to bottom. Alternatively or additionally, the sterilised air preferably serves for the preheating and/or the drying of the at least one container after a heating of the same, if necessary likewise in the sterilisation zone. Synergies can also be achieved in this manner. Therein the preheating of the container can occur before the sterilisation of the container. The reactions killing the microorganisms proceed more quickly at increased temperature. Furthermore, less of the treatment agent condenses in and/or on the container in the form of a mixture of water vapour and hydrogen peroxide. Sterilised air can alternatively or additionally serve to dry the sterilised container, if necessary likewise in the sterilisation zone. Condensate formed during the sterilisation is thereby removed before the filling of the container. At least one part of the sterilised air supplied to the sterilisation zone is, together with the still vaporous hydrogen peroxide, guided away from the sterilisation zone and supplied to the condenser to condense the hydrogen peroxide. It can, however, alternatively or in addition to any step of the preheating and/or drying of the at least one container, also be preferred to blow sterilised air into the sterilisation zone. As a consequence of the gas flow of the sterilised air, an introduction of foreign matter from outside into the sterilisation zone can then be prevented.

The hydrogen peroxide is supplied to the evaporator as an aqueous solution to execute the method simply and to reduce costs. Therefore, the at least one container is then impinged with vaporous hydrogen peroxide and water vapour, as well as if necessary additionally with sterilised air to thin the sterile gas. This means, in particular, that the vaporous hydrogen peroxide is both introduced into the container and comes into contact with the outer side of the container, at least in the region of the opening. The outer sides of the container can also be sterilised as the opening must still be closed after the filling of the container. Otherwise, microorganisms could thereby enter into the container. The hydrogen peroxide solution can therefore, for the sake of simplicity, be supplied to the evaporator from a storage container. The unconsumed part of the hydrogen peroxide, so the part of the hydrogen peroxide which was not converted during the sterilisation, is preferably removed from the sterilisation zone with the non-condensed water vapour and, if necessary the sterilised air. The corresponding gas mixture is subsequently supplied to the condenser in order to partially condense each of the hydrogen peroxide and the water vapour. The gas mixture is therein preferably cooled to a temperature between 35° C. and 95° C. in the condenser. The temperature can be selected depending on the desired hydrogen peroxide concentration in the condensate and/or recovery rate of the hydrogen peroxide. With increasing temperature, less hydrogen peroxide is recovered but a higher hydrogen peroxide concentration is achieved in the condensate.

Preferably the sterilisation zone has a lower end or a base such that the hydrogen peroxide can be removed on the base side. As the hydrogen peroxide is preferably initially led, for the sake of simplicity, from above into the opened container, the vaporous hydrogen peroxide can easily be removed from the sterilisation zone from below without impairing the sterilisation. If a transport device, for example a transport chain, to transport the at least one container through the device, in particular the filling machine, and/or through the sterilisation zone is provided, this is difficult to keep sterile. If the hydrogen peroxide is removed underneath this transport device, additionally a contamination of the aseptic zone by the transport device is prevented.

The economy of the method can be increased if the condenser is operated in such a way that that condensate has a higher hydrogen peroxide concentration than the hydrogen peroxide solution before the evaporator. In order to ensure this, a determined condenser temperature can be adjusted or a control unit can be provided which regulates the condenser temperature by means of the hydrogen peroxide concentration of the condensate. Additionally the mass flow of the sterilised air supplied to the sterilisation zone is eligible as an alternative or additional manipulated variable to regulate the hydrogen peroxide concentration of the condensate. It can, however, also be expedient if the hydrogen peroxide concentration of the condensate is lower than the hydrogen peroxide solution before the evaporator, for example in order to reduce the required quantity of hydrogen peroxide. Then, however, it can be required to remove a part of the water from the condensate and therefore to concentrate the hydrogen peroxide. This can occur using at least one separator to implement a reverse osmosis, a molecular sieve, an evaporator or other separators. Fundamentally, it is preferred from economic viewpoints if the hydrogen peroxide concentration amounts to between 10% by weight and 70% by weight. Therein, is can be preferred for the effective further use of the hydrogen peroxide, if the hydrogen peroxide concentration amounts to at least 15% by weight, at least 20% by weight or at least 25% by weight. Alternatively or additionally, it can, for example for energetic or procedural reasons, be preferable or sufficient if the hydrogen peroxide concentration amounts to no more than 30% by weight, 40% by weight or 50% by weight.

In order to provide a suitable hydrogen peroxide concentration for the evaporation and the sterilisation, the condensate accruing in the condenser can be adjusted to a predetermined hydrogen peroxide concentration between 25% by weight and 50% by weight, more preferably between 30% by weight and 40% by weight, in particular 33% by weight and 37% by weight. This can be achieved particularly simply and cost-effectively if the hydrogen peroxide concentration is thinned back by addition of water, is increased by addition of hydrogen peroxide solution and/or is increased by removal of water. To reduce the regulation expenditure, the adjustment of the hydrogen peroxide concentration preferably occurs in batches. Fundamentally the sterilisation of the at least one container leads to a consumption of hydrogen peroxide. The consumed hydrogen peroxide is therefore preferably replaced, wherein the hydrogen peroxide, for the sake of simplicity, is supplied for example having the concentration which is also supplied to the evaporator. The supply of hydrogen peroxide then requires no or at best a low adaptation of the concentration. Also with regard to the supply of hydrogen peroxide, an implementation in batches is advantageous to reduce the regulation expenditure. A conditioning device can be provided to adjust the concentration of hydrogen peroxide and the filling of the quantity of the hydrogen peroxide. The conditioning can then occur in batches in a storage container, whereby the regulation expenditure can be considerably reduced. Therein it is also preferred to supply the, in particular demineralised, water and the hydrogen peroxide solution from a storage container to the storage container. The use of molecular sieves is particularly preferred to separate water from the condensate in terms of economy and energy. These can, for example, be formed from zeolites and/or carbon and can have a large inner surface, for example larger than 500 $m^2/g$. The pore diameters are fairly uniform and similar to the size of the water molecules to be separated. The molecular sieves which are loaded with water can be regenerated by heating, wherein the water is driven out again.

The condensate accruing in the condenser can be enriched with foreign matter such as dust, components of the container, etc. Therefore it is expedient to filter the condensate. A filter made from polyethylene (PE) or polypropylene (PP) can be used as a filter as these materials are only slightly affected by hydrogen peroxide and have no catalytic influence on the decomposition of hydrogen peroxide. This is even more the case if a sintered polyethylene is used which preferably has a pore size between 10 µm and 200 µm, in particular between 30 µm and 50 µm or between 90 µm and 110 µm. If the filtrate can drain downwards, the filter becomes dry such that the hydrogen peroxide does not react with the filter residue. A further advantage of a sintered filter made from polyethylene consists in the cost-effective production and the simple assembly. Alternatively or additionally, it can be expedient to supply the condensate, in particular after filtration, to an ion exchanger, preferably cation exchanger. Due to the ion exchange in the ion exchanger, for example salt deposits can be reduced or even prevented. In the case of use of a cation exchanger, acids remain in the condensate which contribute to the stabilisation of the hydrogen peroxide. In order to keep the equipment expenditure low, the filtration and/or the ion exchange preferably occurs before the adjustment of the hydrogen peroxide concentration of the solution supplied to the evaporator. Independently of this, the filter device can be a component of the conditioning device in order to bring together the preparation in a manner that is according to the method and compact.

For the filling of the container it is preferred if the at least one container is preheated with hot sterilised air in the sterilisation zone before the impinging with vaporous hydrogen peroxide. Less condensate then results during sterilisation and the hydrogen peroxide does not cool so much, such that high reaction speeds are achieved. Alternatively or additionally, the container sterilised by means of vaporous hydrogen peroxide can be dried with sterilised air. Therefore, condensate is driven out before the filling and it is prevented that hydrogen peroxide remaining in the container oxidises and/or contaminates the food to be filled.

Independently of this, the container is preferably filled with a product in the form of a food after the impinging with the vaporous hydrogen peroxide and the thereby occurring sterilisation. The method is therefore provided in particular for flowable products which can be at least pasty or if necessary liquid as well as if necessary can additionally contain chunky ingredients. The described method is especially suitable to fill drinks in the case of which cycle times which are as low as possible are of particular economic significance due to the quantities to be filled.

The filling of containers in a short amount of time can be favoured if several containers are transported through the aseptic chamber or the sterilisation zone and/or the filling and sealing zone one behind the other with the aid of a transport device. Therefore, short cycle times can be achieved and rejects avoided. The transport device can have cells to receive individual containers for the secure and defined transport of the containers. Therein it is alternatively or additionally constructively particularly simple if the transport device is formed as a transport chain.

Fundamentally, the previously described method is particularly economical to use if a package is used as a container. The package is additionally preferably open upwards in order to simplify the sterilisation and filling. Therein, in particular a cardboard composite package is eligible as a package. Therein it can also be provided that the base is not yet closed before the filling and points upwards. The head of the package is then preferably already closed such that the package can be filled through the base.

If the device is provided with a filter device, the foreign matter contained in the filter device can be separated from the condensed hydrogen peroxide such that an enrichment of corresponding foreign matter is prevented. For this purpose in particular the filter device has an, if necessary sintered, filter made from polyethylene and/or polypropylene, as has already been described previously. The foreign matter can therein in particular be dust or abraded material of the containers to be sterilised.

In order to be able to adjust the concentration of the hydrogen peroxide solution to be supplied to the evaporator such that the hydrogen peroxide concentration of the solution used for sterilisation can be kept approximately constant despite the recirculation of a part of the hydrogen peroxide, the device preferably has a conditioning device or adjustment device to adjust the desired hydrogen peroxide concentration in the condensate. The conditioning device or adjustment device can comprise a thinning device to thin the hydrogen peroxide concentration, and indeed in particular by addition of water. The thinning device can, for this purpose, be connected to a water line or have a storage container with water. Alternatively or additionally, a concentration device can also be provided which serves to increase the hydrogen peroxide concentration. For this purpose, for example, hydrogen peroxide can be added or water can be separated from the condensate. Preferably a molecular sieve is used to separate water. The water can fundamentally, however, also be separated in another manner. The adjustment of the hydrogen peroxide concentration primarily occurs intermittently, so in batches. This simplifies the regulation expenditure. Nevertheless, a regulation device is, however, expedient to monitor the concentration adjustment. Likewise, a continuous adjustment of the hydrogen peroxide concentration can be expedient. Less hydrogen peroxide must then be handled. Additionally, less construction space is required for the apparatus technology.

Alternatively or additionally, the device can have a supply device to replace non-condensed hydrogen peroxide. In this manner, the loss of hydrogen peroxide, in particular as a consequence of the killing of microorganisms and of the hydrogen peroxide proportion leaving the condenser via the gas phase, can be compensated for simply. The supply device therefore preferably comprises a storage container with a hydrogen peroxide solution, the concentration of which can correspond approximately to the concentration of the hydrogen peroxide solution to be supplied to the evaporator.

To simplify the process, it can be preferred if the filter device, the thinning device and/or the supply device are brought together in a conditioning device. The conditioning device can comprise at least one storage container for the conditioning of the hydrogen peroxide solution in batches. Then, after the conditioning of the hydrogen peroxide solution has occurred, the storage container of the hydrogen peroxide solution for the evaporator can be fed from the at least one storage container.

The filling of the container with foods can be implemented in a secure and quick manner if the device, in particular the filling machine, has a preheating device to preheat the at least one container with hot sterilised air, in particular in the sterilisation zone. Then, less condensate results during sterilisation and high reaction kinetics can be ensured which ensures a reliable oxidation of the microorganisms. Alternatively or additionally, a drying device can be provided to dry the sterilised container with sterilised air, in particular in the sterilisation zone. Condensed hydrogen peroxide is then removed, which could otherwise remain in the container in place of the food to be filled. Additionally the hydrogen peroxide would oxidise the food to be filled which can be undesirable. For the sterile filling of the sterilised container, a filling device is provided which is formed to fill the sterilised container with food in the filling and sealing zone. So that even after the filling, no contamination of the filled food takes place, a closing device can be provided to close the filled container, in particular in the filling and sealing zone. The container is then only transported from the filling and sealing zone after closing.

To transport the container, the device, in particular the filling machine, fundamentally has a transport device which can transport, in particular, several containers through the sterilisation zone and/or the filling and sealing zone or the aseptic chamber one after the other. In order to be able to ensure a defined transport of the containers at a defined spatial and temporal distance in order to prevent rejects, the transport device preferably has cells in which individual containers can be introduced and/or held. The cells are therein preferably formed such that the receivers thereof correspond to outer dimensions of the containers which simplifies the receiving of the containers. Alternatively or additionally, the transport device can be formed as a transport chain. This can be led simply in a circle in order to be able to ensure a regular feed and replenishment of the containers.

Fundamentally, it is particularly economical if a package which can be open upwards for simple sterilisation and/or filling is used as a container. Therein, a cardboard composite package in particular is eligible as a package, as has already been described by way of example at the beginning and is known from prior art.

In order to be able to ensure a sterilisation of containers in the described manner with high operational security, at least one control device can be provided which assumes control and/or regulation of individual partial processes and/or of the entire process.

BRIEF DESCRIPTION OF THE DRAWINGS

The invention is explained in more detail below by means of drawings which only represent exemplary embodiments. In the drawings are shown FIG. 1 a detail of a device according to the invention in a schematic depiction and FIG. 2 a method according to the invention in a schematic depiction.

DETAILED DESCRIPTION OF THE INVENTION

Figure 1:
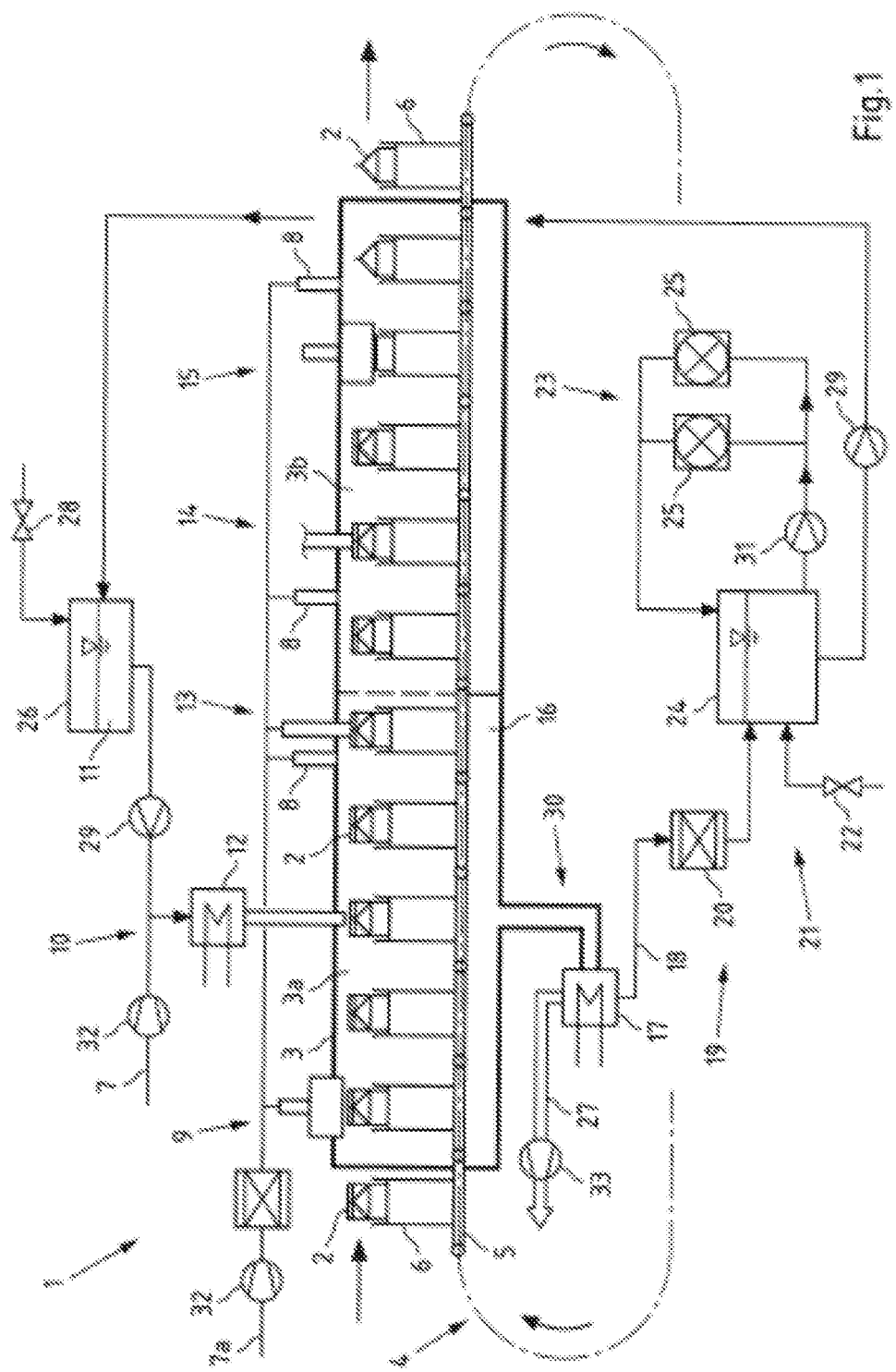

In FIG. 1, a detail of a device 1 to sterilise containers 2 in the form of a filling machine is depicted schematically. The depicted device 1 has an aseptic chamber 3 which comprises a sterilisation zone 3 a and a filling and sealing zone 3b through which a row of containers 2 in the form of packages are transported at least partially one after the other. The transport direction of the containers 2 therein points, as is symbolised by the arrows, from left to right, wherein the transport of the containers 2, however, does not have to occur in a straight line, but can also occur in an arc or even in a circle. The containers 2, in the form of packages, which in particular are cardboard composite packages having at least one cardboard layer, an aluminium layer and outer layers made from a thermoplastic plastic, in particular polyethylene (PE), are transported through the aseptic chamber 3 with the aid of a transport device 4 comprising a transport chain 5. For this purpose, the containers 2 in the form of packages are preferably initially each formed from a cut-to-size package by folding and partially welding or sealing the package material. The package base is thereby formed and closed. The head of the container remains open in order to be able to fill the container. The head of the container could, however, also be closed and the container could be filled through base which is still not closed.

The container 2 is preferably formed to be cuboidal and is passed to the transport device 4 in the form of a transport chain 5 after the forming. Fundamentally, the containers, however, can also have another form. For example, spherical or pyramidal containers are also possible. For this purpose, the transport device 4 has cells 6 into which the containers 2 in the not closed state, which can also be referred to as package blanks in the depicted embodiment, are introduced. The containers 2 or package blanks are then preferably held in a positive manner in the cells 6, such that on the one hand an easy introduction and removal of the containers 2 and on the other hand a defined transport with regard to the speed and the distance of the containers 2 between each other can be ensured. The infinite transport chain 5 is therein driven in a circle.

The transport device 4 is not sterile, such that the aseptic region of the filling and sealing zone 3b only reaches to the transport device 4, which, however, is sufficient for the sterile filling of a food in the filling and sealing zone 3b. In order to prevent a contamination of the containers 2 by the transport device 4, preferably a flow of sterilised air 7a is maintained from top to bottom in the aseptic chamber 3. For this purpose, corresponding sterilised air connections 8 are provided along the aseptic chamber 3 to supply sterilised air 7a. As a consequence of the sterilised air flow, no microorganisms can migrate from the transport device 4 upwards and settle at the upper end of the containers 2.

The sterilisation zone 3a and the filling and sealing zone 3b are separated in the depicted device 1 by a curtain of sterilised air which is blown upwards and flows downwards in a substantially laminar manner. Alternatively or additionally to the curtain, a sluice or a constriction would also be conceivable which just allows the containers into the filling and sealing zone 3b, but which at least tends to retain the atmosphere from the sterilisation zone 3a.

After the entry into the sterilisation zone 3a, the containers 2 are preheated by a preheating device 9 one after the other by blowing with hot sterilised air 7a. In a next station, the containers 2 are impinged with a mixture of water vapour, hydrogen peroxide and, preferably filtered, air 7 by means of a sterilisation device 10 which can be formed as a dosing device or can comprise a dosing device, in order to sterilise the containers 2. For this purpose, in the depicted and in this respect preferred device 1, an aqueous hydrogen peroxide solution 11 with a concentration between 30% by weight and 40% by weight, in particular of approximately 35% by weight, is evaporated on an electrically heated surface in an evaporator 12. The temperature of the vapour amounts to, in the depicted and in this respect preferred device 1, between 250° C. and 300° C., for example 270° C. The vapour is blown from a nozzle together with the filtered air 7 in order to lead the hydrogen peroxide evenly over the surface of the containers 2 to be sterilised. The filtered air 7 therein increases the total volume of the sterilisation gas which amounts, in the depicted and in this respect preferred device 1, to a concentration between 2% by volume and 10% by volume, in particular 2.5% by volume and 8% by volume. Therefore, a sterilisation of the containers 2 can be achieved with a low use of hydrogen peroxide. The hydrogen peroxide reacts on the surface of the container 2 with the microorganisms present there at temperatures between 150° C. and 270° C., in particular approximately 170° C. to 220° C., and thereby kills these.

After the sterilisation of the containers 2, these are dried by impinging with sterilised air 7a via a drying device 13 such that the hydrogen peroxide and condensed water are removed, before the containers 2 are subsequently filled with a food product, in the depicted and this respect preferred device 1 a drink, using a filling device 14. The filled containers 2 are then closed. In the depicted and in this respect preferred device 1, this occurs using a closing device 15 by folding the upper region of the package and sealing the corresponding region, wherein package sections which touch each other are welded to each other. The closed containers 2 are then transported from the aseptic chamber 3 by means of the transport device 4. Subsequently the containers 2 can be removed from the cells 6 of the transport device 4 one after the other.

At the lower end of the sterilisation zone 3a, underneath the transport device 4, the mixture of sterilised air, water vapour and vaporous hydrogen peroxide is removed via a suction box 16. The suction box 16 does not extend, in the depicted and in this respect preferred device 1, under the filling and sealing zone 3b. Therefore, the sterilised air is likewise not removed from the filling and sealing zone 3b, whereby the volume flow removed via the suction box would increase and the hydrogen peroxide concentration would decrease as a consequence of the corresponding thinning. The gas mixture can, for example, have a temperature of between 50° C. and 80° C., in particular between 60° C. and 70° C. The removed gas mixture is then supplied to a condenser 17 in which the water and the hydrogen peroxide are partially condensed. The condenser can be a tube bundle heat exchanger having several tube registers. It is therein preferred if the individual tube registers each operate in the cross-flow and are each flowed through with coolant in series as well as in counter-flow to the gas mixture to be condensed. The gas mixture to be condensed is therein guided in a zigzagged manner from bottom to top through the individual tube registers. Therein, the composition of the gas mixture over the gas flows supplied to the sterilisation zone 3a and/or the at least one temperature of the condenser 17 is selected such that the concentration of the hydrogen peroxide in the condensate 18 amounts to approximately between 30% by weight and 35% by weight. Fundamentally, however, other concentrations can also be expedient, such as for example at least 15% by weight, at least 20% by weight or at least 25% by weight, as well as for example at most 70% by weight, at most 50% by weight or at most 40% by weight.

The condensate 18 is subsequently supplied to a conditioning device 19 in which the condensate 18 is freed from dust and/or other particles from the sterilisation zone 3 in a filter device 20 having a filter made from sintered polyethylene. To clean the filter, this can be periodically backwashed.

The thus cleaned condensate 18 is supplied to an adjustment device 21 to adjust the desired hydrogen peroxide concentration, said adjustment device 21 comprising, in the depicted and in this respect preferred device 1, a thinning device 22 and a concentration device 23. The thinning device 22 has a supply 32 of, preferably demineralised, water in a storage container 24, in which the condensate 18 from the condenser 17 can be thinned by addition of water. The hydrogen peroxide concentration is thereby preferably adjusted to a value between 30% by weight and 40% by weight, in particular approximately 35% by weight. The concentration device 23 comprises at least one absorption unit 25 comprising molecular sieves for the absorption of water which is driven out again from the molecular sieves in a separate step. The concentrated hydrogen peroxide solution can be led back into the storage container 24. The conditioning of the hydrogen peroxide solution occurs intermittently and in batches.

The hydrogen peroxide solution with the adjusted concentration is guided from the storage container 24 to an intermediate storage 27 in which further hydrogen peroxide solution is supplied through a supply device 28 to compensate for the consumed hydrogen peroxide and the hydrogen peroxide contained in the gas phase 25 leaving the condenser 17. This preferably occurs via a hydrogen peroxide solution of predetermined concentration which can correspond to the concentration which is adjusted in the storage container 24.

Additionally, in the depicted and in this respect preferred device 1, surfaces of the device 1 which come into contact with hydrogen peroxide can consist of steel of material number 1.4404 or 1.4571 (each V4A), of polyethylene (PE), of polypropylene (PP) or of glass. Alternatively, the contact surfaces can be passivated and/or heated. Incidentally, the temperature of the hydrogen peroxide solution between the condenser 17 and the evaporator 12 can be kept from a temperature level of less than 50° C. in order to prevent an evaporation of hydrogen peroxide. Alternatively or additionally, organic and/or inorganic stabilisers can be added to the hydrogen peroxide solution which can also be evaporated and/or leave the evaporator 12 as aerosols. In the depicted and in this respect preferred device 1, pumps are provided to convey the condensate 18 from the condenser 17 to the intermediate storage 27 and furthermore to the evaporator 12. These pumps 29 can form a supply unit or be a part thereof. Alternatively or additionally, the conditioning device 19 can also completely or partially part of the supply unit. The same applies for corresponding tube lines or similar which have previously not been referred to in detail, but can be gleaned without any problems from FIG. 1. Additionally, a removal device 30 is provided to remove water vapour, vaporous hydrogen peroxide and sterilised air from the sterilisation zone 3a or the suction box 16. A further pump 31 is provided to operate the concentration device 23.

Figure 2:
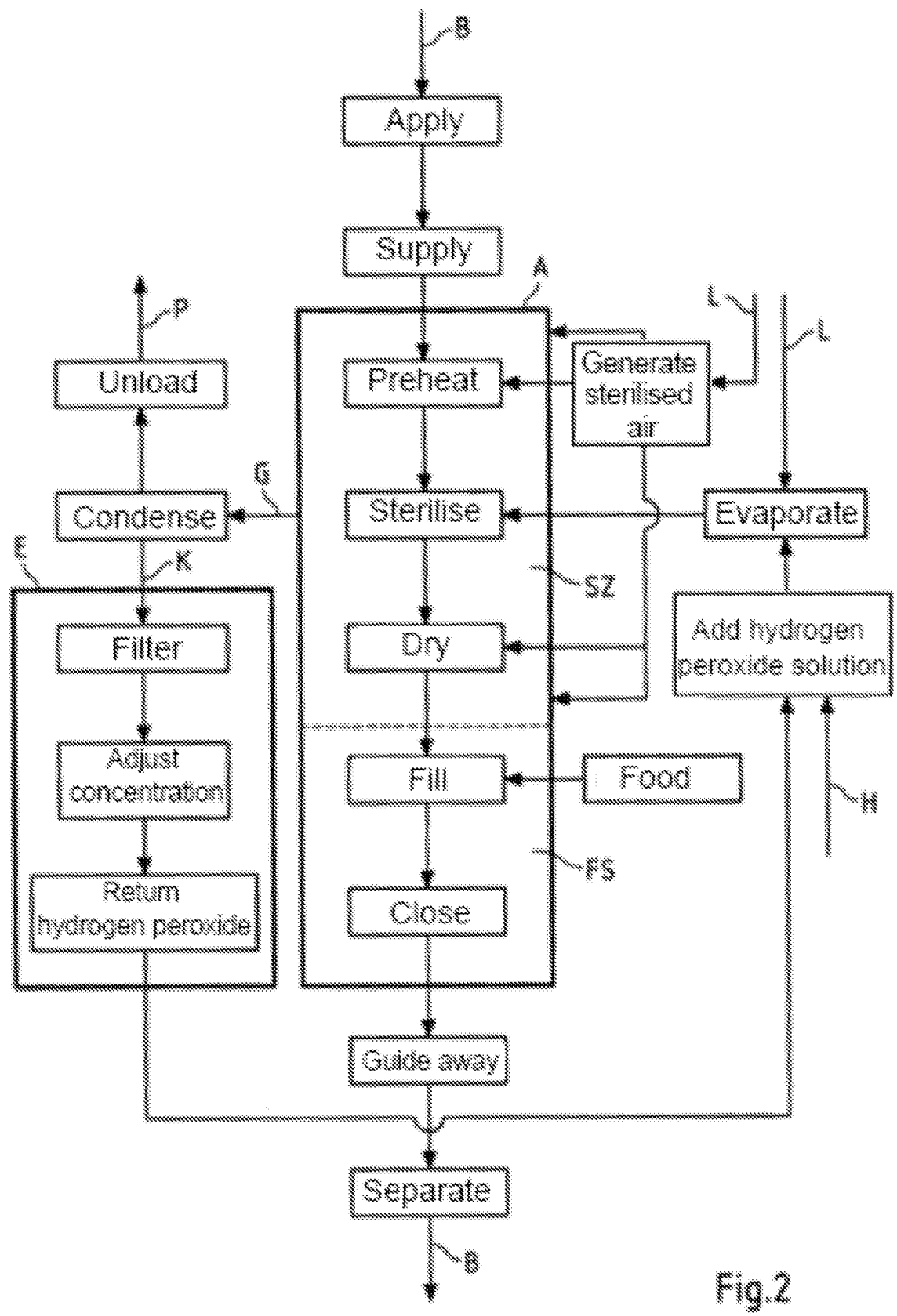

The method to operate the previously described device 1 is depicted schematically as a block flow diagram in FIG. 2. Therein, the method steps occurring in the aseptic chamber or in direct connection with the aseptic chamber are arranged in a frame A representing the aseptic chamber. The processing steps with regard to a container B are arranged vertically one below the other. Initially, the application of the container B to the transport unit which assumes the transport of the container B through the aseptic chamber A occurs. Then the supply of the container B into the sterilisation zone SZ occurs. In the sterilisation zone SZ, the preheating of the container B with hot sterilised air occurs; the sterilised air is initially produced from roughly purified air L by filtering the same. The sterilised air is also blown into the aseptic chamber A at further points.

After the preheating of the container B, the sterilisation of the preheated container B occurs with a mixture of roughly purified air, water vapour and vaporous hydrogen peroxide. In a further step, the sterilised container B is transferred into the filling and sealing zone FS and there is filled with a food from a store. Subsequently, the container B is closed and is sealed in a sealing station by ultrasonic welding. The thus sealed container is then guided away from the aseptic chamber A with the aid of a transport device. Then a separation of the completed container B from the transport device occurs.

The contained gas mixture G of water vapour, vaporous hydrogen peroxide and sterilised air is removed from the sterilisation zone SZ and supplied to a condenser. The condensate K and a gas phase P leaves the condenser, said gas phase being removed, in the depicted and in this respect preferred device, as an exhaust gas. The gas phase P contains, besides the air removed from the sterilisation zone SZ, further residue of water vapour and hydrogen peroxide. The condensate K is passed into a conditioning device E, symbolised by a frame, in which a filter device is provided, which filters the condensate K in order to separate solids. Subsequently the purified condensate reaches a storage container to condition the purified condensate, in particular to adjust the hydrogen peroxide concentration of the condensate. The concentration of the hydrogen peroxide in the condensate can be reduced via a thinning device by means of the addition of, in particular demineralised, water. Alternatively or additionally, the hydrogen concentration of the condensate is increased by the water of the condensate being partially separated and indeed preferably just to the extent that the desired hydrogen peroxide concentration can be provided. The correspondingly conditioned hydrogen peroxide solution is then replenished and dispensed to an intermediate storage, from which the hydrogen peroxide solution can be continuously supplied to the evaporator. Consumed hydrogen peroxide can be replaced in the intermediate storage by addition of a fresh hydrogen peroxide solution H of suitable concentration of hydrogen peroxide. The concentration of the fresh hydrogen peroxide solution therein corresponds approximately to the concentration of the conditioned condensate which is supplied to the intermediate storage. The condensate is supplied to the evaporator again to sterilise further containers.

The invention claimed is:

1. A method to sterilise containers to receive flowable foods in a filling device comprising:
   evaporating a hydrogen peroxide solution in an evaporator;
   impinging at least one container with the vaporous hydrogen peroxide in a sterilisation zone;
   removing, at least partially, an unconsumed part of the vaporous hydrogen peroxide from the sterilisation zone;
   condensing, at least partially, the removed vaporous hydrogen peroxide in a condenser, wherein the condenser is operated in such a way that a condensate has a higher or lower hydrogen peroxide concentration than the hydrogen peroxide solution before the evaporation; and
   supplying the condensed hydrogen peroxide to the evaporator.

2. The method according to claim 1, in which sterilised air is supplied to the sterilisation zone to preheat or to dry the at least one container, and
   in which the sterilised air is at least partially removed from the sterilisation zone with the vaporous hydrogen peroxide and is supplied to the condenser.

3. The method according to claim 1, in which an aqueous hydrogen peroxide solution is evaporated in the evaporator,
   in which the unconsumed part of the vaporous hydrogen peroxide and the water vapour are each at least partially removed from the sterilisation zone and are at least partially condensed in a condenser.

4. The method according to claim 1, in which the hydrogen peroxide is removed on a base side below a transport device to transport the at least one container through the device.

5. The method according to claim 1, in which the condensate accruing in the condenser is adjusted to a predetermined hydrogen peroxide concentration between 25% by weight and 50% by weight and in which the hydrogen peroxide concentration of the concentrate is adjusted by thinning.

6. The method according to claim 1, in which the condensate accruing in the condenser is filtered to separate foreign matter or is supplied to an ion exchanger for ion exchange.

7. The method according to claim 1, in which the at least one container is preheated with hot sterilised air in the sterilisation zone before the impinging with vaporous hydrogen peroxide, is dried with sterilised air after the impinging with the vaporous hydrogen peroxide, is filled with a flowable product after the impinging with the vaporous hydrogen peroxide, and is closed after the filling.

8. The method according to claim 1, in which a plurality of containers are transported through the sterilisation zone one after the other with the aid of a transport device having cells to receive individual containers.

9. The method according to claim 1, in which the container comprises a cardboard composite package.

10. The method according to claim 1, in which the hydrogen peroxide concentration is between 10% and 70% by weight.

11. The method according to claim 5, in which the hydrogen peroxide concentration is between 30% and 40% by weight.

12. The method according to claim 5, in which the hydrogen peroxide concentration of the concentrate is adjusted by thinning with water or by concentrating using a molecular sieve.

13. The method according to claim 6, in which the ion exchanger comprises a cation exchanger.

* * * * *